US011324854B2

(12) United States Patent
Solimando et al.

(10) Patent No.: US 11,324,854 B2
(45) Date of Patent: May 10, 2022

(54) RESORBABLE IMPLANTABLE DEVICE BASED ON CROSSLINKED GLYCOSAMINOGLYCANS, AND PROCESS FOR THE PREPARATION THEREOF

(71) Applicant: Altergon SA, Lugano (CH)

(72) Inventors: Nicola Solimando, Pietradefusi (IT); Maurizio Pagliuca, Pietradefusi (IT)

(73) Assignee: Altergon SA, Lugano (CH)

( * ) Notice: Subject to any disclaimer, the term of this patent is extended or adjusted under 35 U.S.C. 154(b) by 42 days.

(21) Appl. No.: 16/763,856

(22) PCT Filed: Nov. 14, 2018

(86) PCT No.: PCT/IB2018/058965
§ 371 (c)(1),
(2) Date: May 13, 2020

(87) PCT Pub. No.: WO2019/097427
PCT Pub. Date: May 23, 2019

(65) Prior Publication Data
US 2021/0052769 A1    Feb. 25, 2021

(30) Foreign Application Priority Data
Nov. 17, 2017  (IT) .................. 102017000131879

(51) Int. Cl.
| A61L 27/20 | (2006.01) |
| A61L 27/52 | (2006.01) |
| A61L 27/58 | (2006.01) |
| C08J 3/075 | (2006.01) |
| C08L 5/08 | (2006.01) |
| A61K 31/167 | (2006.01) |

(52) U.S. Cl.
CPC ............ *A61L 27/20* (2013.01); *A61L 27/52* (2013.01); *A61L 27/58* (2013.01); *C08J 3/075* (2013.01); *C08L 5/08* (2013.01); *A61K 31/167* (2013.01); *A61L 2400/06* (2013.01); *C08J 2305/08* (2013.01)

(58) Field of Classification Search
CPC .......... A61L 27/52; A61L 27/58; A61L 27/00; A61L 2400/06; A61L 27/20; A61K 31/167; A61K 31/726; A61K 31/728; C08J 3/075; C08L 5/08
See application file for complete search history.

(56) References Cited

U.S. PATENT DOCUMENTS

| 4,716,454 A | 12/1987 | Oldershaw et al. |
| 9,347,079 B2 | 5/2016 | Pagliuca et al. |
| 2011/0077737 A1* | 3/2011 | Stroumpoulis ......... A61P 17/00 623/8 |
| 2012/0071437 A1* | 3/2012 | Stroumpoulis ......... A61L 27/20 514/54 |
| 2017/0266344 A1 | 9/2017 | Yu et al. |

FOREIGN PATENT DOCUMENTS

| EP | 3194452 A1 | 7/2017 |
| KR | 20160060227 A | 5/2016 |

OTHER PUBLICATIONS

Search Report and Written Opinion of PCT/IB2018/058965 dated Mar. 28, 2019.

* cited by examiner

*Primary Examiner* — Carlos A Azpuru
(74) *Attorney, Agent, or Firm* — Silvia Salvadori, P.C.; Silvia Salvadori

(57) ABSTRACT

Disclosed is a process for the preparation of hydrogels consisting of crosslinked glycosaminoglycans, which comprises: a) reacting at least one hybrid cooperative complex obtained by heating aqueous solutions of low- and high-molecular-weight glycosaminoglycans at 80-160° C. with a diepoxide as crosslinker in a ratio with the complex ranging between 0.1 and 1 equivalents, preferably between 0.2 and 0.4 equivalents, the concentration by weight of the complex in the solution ranging between 1% and 15%, preferably between 2% and 10%; b) purifying by dialysis, ultrafiltration and diafiltration.

9 Claims, No Drawings

RESORBABLE IMPLANTABLE DEVICE BASED ON CROSSLINKED GLYCOSAMINOGLYCANS, AND PROCESS FOR THE PREPARATION THEREOF

This application is a U.S. national stage of PCT/EP2018/058965 filed on 14 Nov. 2018, which claims priority to and the benefit of Italian Application No. 102017000131879 filed on 17 Nov. 2017, the contents of which are incorporated herein by reference in their entireties.

The present invention relates to a process for the preparation of hydrogels consisting of crosslinked hybrid cooperative complexes of glycosaminoglycans. The invention also relates to the implantable devices obtained by said process, which are characterised by high resistance to hyaluronidases and optimum rheological properties which remain stable over time. The devices according to the invention can be formulated in monophasic and/or biphasic combinations, optionally in combination with a local anaesthetic.

PRIOR ART

Due to their rheological, biocompatibility and biodegradability properties, glycosaminoglycans, especially hyaluronic acid and the salts thereof, are used in various biomedical fields, such as ophthalmology, in orthopaedics to restore the functionality of the synovial fluid, and in dermocosmetics and aesthetic and regenerative medicine for the formulation of intradermal fillers.

The physiological and physicochemical properties of hyaluronic acid are associated with its molecular weight. Polymer chains with a high enough weight, like those present in synovial fluid, have a high viscosity which forms the basis of their shock-absorbing ability and lubricating property. An undesirable reduction in molecular weight, such as that due to fragmentation of the polymer chains in the case of enzymatic degradation by specific enzymes (hyaluronidases), leads to loss of the characteristic properties of hyaluronic acid.

A set of semi-synthetic derivatives, obtained by crosslinking the hyaluronic acid chains, has been developed for this reason. The crosslinked derivatives are more resistant to enzymatic degradation. Hyaluronic acid crosslinking processes are described in WO 2010/015900, EP 2 236 529, EP 1 303 542 and U.S. Pat. No. 7,741,476.

Hybrid cooperative complexes obtained by heating aqueous solutions of low and high-molecular-weight glycosaminoglycans at 80-160° C. were described in WO2012032151. Said complexes, characterised by low viscosity and constant rheological properties, have been used as active ingredients of ophthalmic compositions (WO 2017016873).

DESCRIPTION OF THE INVENTION

A crosslinking process for hybrid cooperative complexes of glycosaminoglycans has now been found which allows to produce implantable hydrogels characterised by high viscosity at rest (ensuring excellent restriction to the application site, without undesirable spreading into the tissues) and low viscosity during injection, consequently leading to easy extrudability and better compliance with treatments.

The hydrogels obtained by the process according to the invention are characterised by high values of modulus of elasticity G', ranging between 200 Pa and 500 Pa, and elasticity values, ranging between 75% and 95%, with excellent mechanical properties, excellent bulking properties, good longevity and improved resistance to enzymatic degradation, especially to the action of hyaluronidases.

Surprisingly, indeed, when said hybrid complexes (as opposed to hyaluronic acid or linear glycosaminoglycans) are crosslinked, the modulus of elasticity G' of the final hydrogel is significantly higher than that obtained by the standard reactions described in the literature, wherein HA, or mixtures of HA not subjected to thermal pre-treatment, is used.

The process of the invention involves crosslinking the hybrid complexes described in WO 2012032151 with small amounts of diepoxides followed by purification by dialysis, ultrafiltration and diafiltration.

The hybrid complexes are obtained by heating the mixture of a first component selected between low-molecular-weight hyaluronic acid, chondroitin and chondroitin sulphate, and a second component consisting of high-molecular-weight hyaluronic acid, at a temperature ranging between T 80° C. and 160° C., preferably between 80° C. and 120° C., for a reaction time ranging between 10 min. and 30 min., followed by rapid cooling to 20/25° C. in 5-15 min.

The concentration by weight of the first component with low molecular weight ranges between 0.1 and 50%, and the concentration by weight of the second component with high molecular weight ranges between 0.01 and 10%.

The use of hybrid complexes of glycosaminoglycans, especially of hyaluronic acid, allows to increase the stability of the three-dimensional crosslinked structure after crosslinking, guaranteeing better, longer-lasting rheological properties.

In particular, the process of the invention comprises:

a) reacting at least one hybrid cooperative complex obtained by heating aqueous solutions of low- and high-molecular-weight glycosaminoglycans at 80-160° C., preferably between 80° C. and 120° C., with a diepoxide as crosslinker, preferably 1,4-butanediol-diglycidyl-ether, in a ratio with the complex ranging between 0.1 and 1 equivalents, preferably between 0.2 and 0.4 equivalents, the concentration by weight of the complex in the solution ranging between 1% and 15%, preferably between 2% and 10%;

b) purifying by dialysis, ultrafiltration and diafiltration.

The reaction is conducted at a temperature ranging between 10° C. and 50° C., preferably between 15° C. and 30° C., for reaction times ranging between 2 h and 48 h, preferably between 12 h and 24 h.

The preferred glycosaminoglycans are high and low-molecular-weight hyaluronic acid.

"Low-molecular-weight hyaluronic acid" means a hyaluronic acid having a molecular weight Mw, determined by size exclusion chromatography (SEC) and/or SEC-TDA, ranging between $50 \cdot 10^3$ Da and $900 \cdot 10^3$ Da, while "high-molecular-weight hyaluronic acid" means a hyaluronic acid having a molecular weight Mw, again determined by SEC and/or SEC-TDA, ranging between $1 \cdot 10^6$ Da and $3 \cdot 10^6$ Da. Alternatively, the low-molecular-weight glycosaminoglycan can be chondroitin or chondroitin sulphate with a molecular weight Mw ranging between 5,000 and 150,000 Da.

Ultrapure hyaluronic acid obtained by the process disclosed in U.S. Pat. No. 9,347,079 or EP2870255 and available on the market under the trademark Shyalt® is particularly preferred.

The process of the invention can also be performed starting with multiple hybrid complexes, typically between 1 and 4 different complexes. For example, a complex obtained by heating low- and high-molecular-weight hyaluronic acids as defined above can be simultaneously crosslinked with a complex obtained by heating chondroitin (the ultrapure chondroitin obtained by the process described in U.S. Pat. No. 8,592,186 is particularly preferred) or chondroitin sulphate and high-molecular-weight hyaluronic acid as defined above. The use of multiple complexes allows fine regulation of the rheological properties of the hydrogel, which can thus be optimised for the intended cosmetic or therapeutic uses.

The weight ratio between the low-molecular-weight glycosaminoglycan and the high-molecular-weight glycosaminoglycan can vary within a wide range, for example between 0.1 and 1. A weight ratio of 0.5 is preferred.

The preferred conditions for the crosslinking reaction involve a highly effective mixing system which guarantees the maximum interaction of the complexes in the reaction, due to a descending and ascending force of 100N-700N. The slow, variable stirring at which the reaction takes place ranges between 10 rpm and 120 rpm, preferably between 10 rpm and 50 rpm, with a reactor geometry expressed as diameter/height ratio in the 0.5 to 1.5 range.

The combination of said parameters guarantees an efficient, effective degree of crosslinking using a minimal amount of crosslinking agent, with uniform distribution of the bonds.

The purification stages are conducted at temperature gradients ranging between 10° C. and 58° C., preferably between 20° C. and 50° C.; ultrafiltration is advantageously conducted with 1 to 10 diafiltration volumes at a permeation rate ranging between 0.1 L/h and 10 L/h, with ΔP between 1 and 2 bars, using hollow-fibre membranes with a cut-off between 250 and 750 KDa.

Cellulose membranes with a cut-off between 10 KDa and 50 KDa are preferably employed for the dialysis step, using purified water or phosphate buffer with an osmolarity ranging between 200 mOsm/L and 400 mOsm/L as dialysis medium.

The purification stages are conducted for a time sufficient to remove undesirable micropollutants (BDDE, metals, etc).

The application of said techniques guarantees high purity and therefore excellent safety of the product in vivo, with an average residual crosslinking agent content ranging between 25 ppb and 100 ppb, which is considerably lower than the specification limits universally adopted (≤2000 ppb) for the other devices currently available on the market.

The reaction product, i.e. crosslinked hydrogel, is also filtered to standardise it to a standard size ranging between 45 μm and 450 μm, depending on its final use in vivo.

The hydrogel, having different degrees of crosslinking, can be formulated in the final device in aliquots ranging between 1% and 100%, according to the specific requirements for human use, with different final concentrations of hybrid complexes of crosslinked Ha ranging between 1.5% and 4%. Surprisingly, even those with the highest concentrations are easily extruded, and consequently they are very practical to use, with good patient compliance.

The hydrogels obtained by the process of the invention are suitably formulated in the form of implantable devices, for example in phosphate buffer or saline solution, for application in the medical, surgical, aesthetic, orthopaedic, dental, ophthalmic and dermocosmetic fields.

In the implantable devices according to the invention, hyaluronic acid, chondroitin or cellulose derivatives (carboxymethylcellulose, hydroxypropyl methylcellulose, ethylcellulose and the like), whose cooperation considerably increases resistance to hyaluronidases, can be optionally added to the hydrogels.

The addition of a local anaesthetic such as procaine, mepivacaine, benzocaine, ethyl chloride and preferably lidocaine hydrochloride, in concentrations ranging between 0.1% and 3%, can be useful to reduce the immediate pain sensation and numb the treated area.

Example 1: One-Complex Reaction

Preparation of Complex 1:

27.42 g of sodium hyaluronate (LOD 9.7%) with an intrinsic viscosity of 2.1 m$^3$/Kg and 27.12 g of sodium hyaluronate (LOD 8.5%) with an intrinsic viscosity of 3.0 m$^3$/Kg were dissolved by mechanical stirring in 395.45 ml of water. The solution was brought to the temperature of 90° C. for 15 minutes, and rapidly cooled to the temperature of 25° C.

Crosslinking Reaction:

The solution of Complex 1 was transferred to a thermostated container equipped with mechanical stirring, and 50 ml of an 0.25N solution of sodium hydroxide was added. 11.7 ml of a 95% BDDE solution (0.5 equivalents) was added after about 3 hours' stirring. The reaction takes place at a controlled temperature (30±5° C.), with stirring at 40±5 rpm for 12 hours and stirring at 25±5 rpm for a further 12 hours.

The crosslinked product was neutralised to pH 7.4 by adding an HCl solution, then dialysed, diafiltered (5 volumes) and dialysed again.

The hydrogel was formulated by adding 0.3% lidocaine hydrochloride, then adjusted to a concentration of 25 mg/g and mechanically homogenised.

The product underwent standardising filtration of 450 μm.

The hydrogel was introduced into vials and sterilised in the autoclave.

Modulus of elasticity G': 350 Pa.

Elasticity: 82%.

Extrusion force: 35 N.

Example 2: Two-Complex Reaction

Preparation of Complex 1:

13.71 g of sodium hyaluronate (LOD 9.7%) with an intrinsic viscosity of 2.1 m$^3$/Kg and 13.56 g of sodium hyaluronate (LOD 8.5%) with an intrinsic viscosity of 3.0 m$^3$/Kg were dissolved by mechanical stirring in 197.72 ml of water. The solution was brought to the temperature of 90° C. for 15 minutes, and rapidly cooled to the temperature of 25° C.

Preparation of Complex 2:

13.71 g of sodium hyaluronate (LOD 9.7%) with an intrinsic viscosity of 2.1 m$^3$/Kg and 13.68 g of sodium hyaluronate (LOD 9.5%) with an intrinsic viscosity of 0.2 m$^3$/Kg were dissolved by mechanical stirring in 197.6 ml of water. The solution was brought to the temperature of 90° C. for 15 minutes, and rapidly cooled to the temperature of 25° C.

Crosslinking Reaction:

The solutions of Complex 1 and Complex 2 were transferred to a single thermostated container equipped with mechanical stirring, and 50 ml of an 0.25 N solution of sodium hydroxide was added. 11.7 ml of a 95% BDDE solution (0.5 equivalents) was added after about 3 hours' stirring. The reaction takes place at a controlled temperature (30±5° C.), with stirring at 40±5 rpm for 12 hours and stirring at 25±5 rpm for a further 12 hours.

The crosslinked product was neutralised to pH 7.3 by adding an HCl solution, then dialysed, diafiltered (5 volumes) and dialysed again.

The hydrogel was formulated by adding 0.3% lidocaine hydrochloride, then adjusted to a concentration of 25 mg/g and mechanically homogenised.

The product underwent standardising filtration of 450 µm.

The hydrogel was introduced into vials and sterilised in the autoclave.

Modulus of elasticity G': 292 Pa.
Elasticity: 85%.
Extrusion force: 25 N.

Example 3: Two-Complex Reaction

Preparation of Complex 1:

13.71 g of sodium hyaluronate (LOD 9.7%) with an intrinsic viscosity of 2.1 m$^3$/Kg and 13.56 g of sodium hyaluronate (LOD 8.5%) with an intrinsic viscosity of 3.0 m$^3$/Kg were dissolved by mechanical stirring in 197.72 ml of water. The solution was brought to the temperature of 90° C. for 15 minutes, and rapidly cooled to the temperature of 25° C.

Preparation of Complex 2:

13.71 g of sodium hyaluronate (LOD 9.7%) with an intrinsic viscosity of 2.1 m$^3$/Kg and 13.68 g of sodium hyaluronate (LOD 9.5%) with an intrinsic viscosity of 0.2 m$^3$/Kg were dissolved by mechanical stirring in 197.6 ml of water. The solution was brought to the temperature of 90° C. for 15 minutes, and rapidly cooled to the temperature of 25° C.

Crosslinking Reaction:

The solutions of Complex 1 and Complex 2 were transferred to a single thermostated container equipped with mechanical stirring, and 50 ml of an 0.25 N solution of sodium hydroxide was added. 4.7 ml of a 95% BDDE solution (0.2 equivalents) was added after about 3 hours' stirring. The reaction takes place at a controlled temperature (30±5° C.), with stirring at 40±5 rpm for 12 hours and stirring at 25±5 rpm for a further 12 hours.

The crosslinked product was neutralised to pH 7.3 by adding an HCl solution, then dialysed, diafiltered (5 volumes) and dialysed again.

The hydrogel was formulated by adding 0.3% lidocaine hydrochloride, then adjusted to a concentration of 25 mg/g and mechanically homogenised.

The product underwent standardising filtration of 450 µm.

The hydrogel was introduced into vials and sterilised in the autoclave.

Modulus of elasticity G': 250 Pa.
Elasticity: 79%.
Extrusion force: 19 N.

The invention claimed is:

1. A process for the preparation of hydrogels consisting of crosslinked glycosaminoglycans which comprises:
   a) reacting an aqueous solution of at least one hybrid cooperative complex between a first component selected from low-molecular-weight hyaluronic acid, chondroitin and chondroitin sulphate and a second component consisting of high-molecular-weight hyaluronic acid with a diepoxide as crosslinker in an 0.1 to 1 equivalent ratio to the complex, the weight concentration of the complex in the solution ranging from 1% to 15%;
   b) purifying by dialysis, ultrafiltration and diafiltration,
   wherein:
   the hybrid cooperative complex is prepared by subjecting the aqueous solution of a mixture of said first and second components to heat treatment at 80-160° C. for a time ranging between 10 and 30 minutes, followed by cooling to 20-25° C. in a time ranging between 5 and 15 minutes;
   the concentration by weight of the first component with low molecular weight ranges between 0.1 and 50%, and the concentration by weight of the second component with high molecular weight ranges between 0.01 and 10%;
   wherein the molecular weight of the low-molecular-weight hyaluronic acid ranges from 50·103 Da to 900·103 Da, the molecular weight of the chondroitin or chondroitin sulphate ranges from 5000 to 150,000 Da, and the molecular weight of the high-molecular-weight hyaluronic acid ranges from 1·106 Da to 3·106 Da (MW obtained by SEC and/or SEC-TDA),
   wherein the ultrafiltration is carried out with 1 to 10 diafiltration volumes at a permeation rate ranging from 0.1 L/h to 10 L/h, with ΔP from 1 to 2 bars, using a hollow fibre membrane with cut-off from 250 to 750 KDa.

2. The process according to claim 1 wherein the reaction is carried out at a temperature ranging from 10° C. to 50° C., for reaction times ranging from 2 h to 48 h.

3. The process according to claim 1 wherein the number of hybrid complexes is 1 to 4.

4. The process according to claim 1 wherein both the glycosaminoglycans are high- and low-molecular weight hyaluronic acid.

5. The process according to claim 1 wherein the low-molecular-weight glycosaminoglycan is chondroitin or chondroitin sulphate.

6. The process according to claim 1 wherein the diepoxide is 1,4-butanediol-diglycidyl-ether.

7. The process according to claim 1 wherein the purification steps are carried out at temperature gradients ranging from 10° C. to 58° C.

8. The process according to claim 1 wherein dialysis is carried out with cellulose membranes with cut-off ranging from 10 KDa to 50 KDa and using purified water or phosphate buffer with osmolarity ranging from 200 mOsm/L to 400 mOsm/L as dialysis medium.

9. The process according to claim 7, wherein the purification steps are carried out at temperature gradients ranging from 20° C. to 50° C.

* * * * *